April 4, 1972 MARIE-LOUISE MEILLAND Plant Pat. 3,095
ROSE PLANT
Filed Feb. 25, 1970
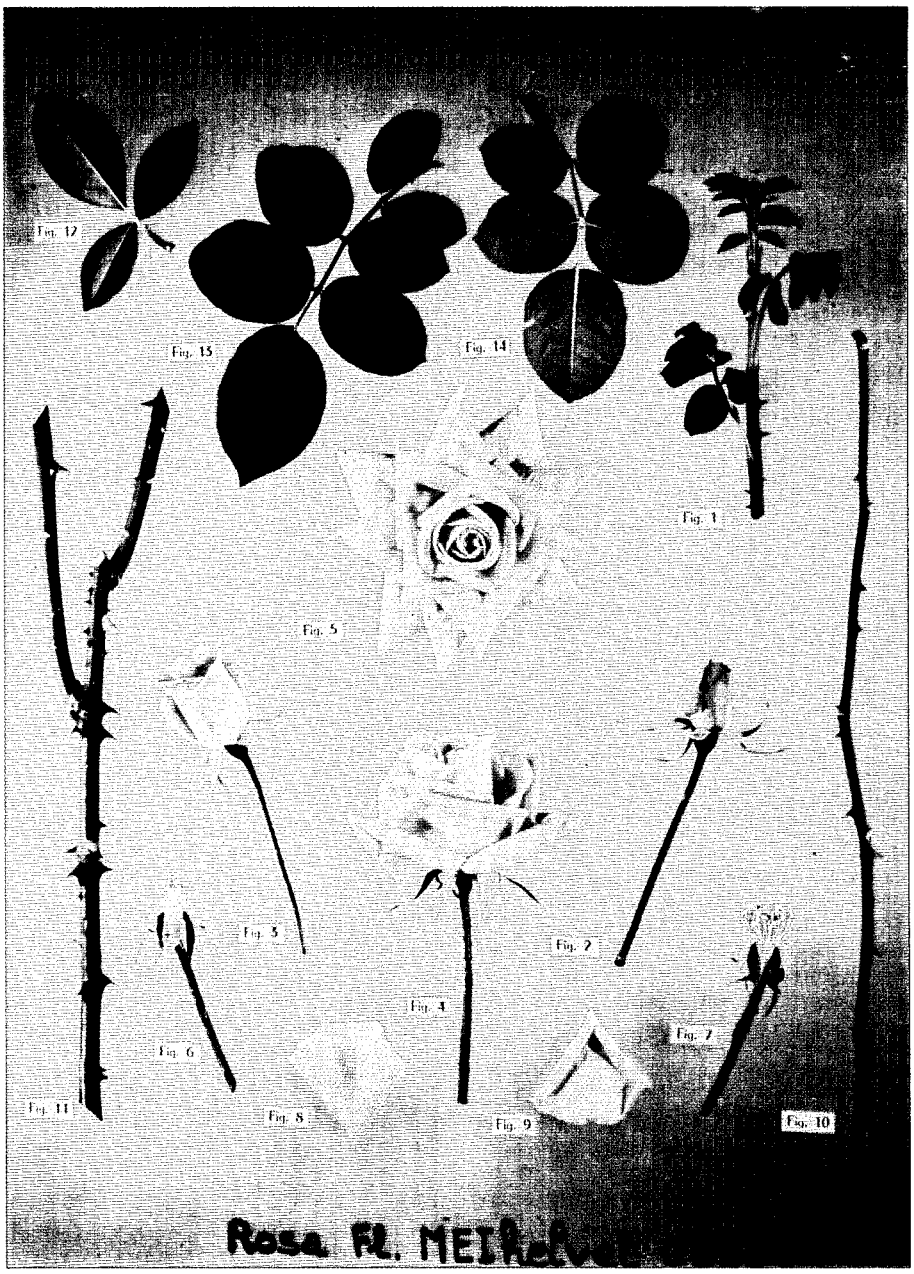
Inventor
Marie-Louise Meilland
By
Burns, Doane, Benedict, Swecker & Mathis
Attorneys

United States Patent Office

Plant Pat. 3,095
Patented Apr. 4, 1972

3,095
ROSE PLANT

Marie-Louise Meilland, Cap d'Antibes, France, assignor to The Conard-Pyle Company, West Grove, Pa.

Filed Feb. 25, 1970, Ser. No. 14,249
Claims priority, application France, Dec. 3, 1969, 6906632
Int. Cl. A01h *5/00*
U.S. Cl. Plt.—18 1 Claim

ABSTRACT OF THE DISCLOSURE

A rose plant of the grandiflora class obtained from crossing Zambra (Plant Pat. No. 2140) with a seedling of Baccara (Plant Pat. No. 1367) crossed with Message (known in the United States as White Knight) (Plant Pat. No. 1359).

SUMMARY OF THE INVENTION

The present invention is a variety of rose plant, of the grandiflora class, with Porcelain Rose double flowers, which is distinguishable from the varieties known up to date, in that class and this kind of color, because of the following characteristics:

freshness, stability and originality of the color of its blooms;
the exceptionally elegant form of these blooms;
its excellent aptitude to being grown under glass (very few buds to be nipped, great productive capacity)
cut flowers lasting a long time in a vase;
dense foliage, wide, and most resistant to fungus diseases.

In view of the characteristics mentioned above, the present invention answers the needs of the horticultural industry concerning the production of cut flowers, as well as the ornamentation of parks and gardens.

The aim was to create a variety which would derive the aforementioned advantages from a genetic combination bringing in two genitors, in their common descent, having the appearance of the characters sought.

The rose chosen as female genitor (seed parent) was the variety Zambra (Plant Pat. No. 2140); the one chosen as male genitor (pollen) was the product of the pollination of the variety Baccara (Plant Pat. No. 1367, by the variety Message (known in the United States as White Knight) (Plant Pat. No. 1359).

The operation of artificial pollination performed can thus be expressed by the following schematic formula: Zambra × (Baccara × Message).

From the fruits formed by this guided pollination, seeds were extracted, whose cells were the result of the combination of factors which existed in the cells of the genitors, and in view of which these genitors had precisely been chosen.

After having sown the above-mentioned seeds, there were obtained 760 small plants, physically and biologically distinct from one another.

After having discarded all the deficient or abnormal plants, or plants whose characters were too remote from the ones desired, the remaining plants were grafted in order to provide plants which were, in every respect, in conformity with those produced and commercialized by professional nurserymen.

Then, a selective study was undertaken of the industrial plants thus formed and during this study there were eliminated systematically all the rose plants which had been grafted, with the exception of one only, which came closest to the aim in view.

This rose plant had very elegant flowers, Porcelain Rose touched up with Begonia Rose in depth, of great originality and remarkable stability; they also kept a long time when cut. Moreover, the plant had a dense foliage, wide, and most resistant to fungus diseases.

Technical tests (grafting with started eye-buds, dormant eye-buds, on various understocks, in heated or cold greenhouses, etc.) were then made in order to check the behavior of the variety which had just been created.

The results were conclusive and underlined the importance of creating this variety with a view to its industrial exploitation by horticulturists for the production of cut flowers, and by professional nurserymen for the ornamentation of parks and gardens.

BRIEF DESCRIPTION OF DRAWINGS

The accompanying drawings show typical specimens of the vegative growth and flower of my new variety in different stages of development and as depicted in color as nearly true as it is reasonably possible to make the same in a color illustration of this character, and wherein:

FIG. 1 is a specimen of young shoot;
FIG. 2 is a specimen of a bud when the sepals open;
FIG. 3 is a specimen of a bud when the petals open;
FIG. 4 is a specimen of a flower when opening;
FIG. 5 is a specimen of a fully open flow, flat view;
FIG. 6 is a specimen of a receptacle showing the disposition of the pistils;
FIG. 7 is a specimen of a receptacle showing the disposition of the stamens;
FIG. 8 is a specimen of a petal of the exterior periphery, outside view;
FIG. 9 is a specimen of a petal of the exterior periphery, outside view;
FIG. 10 is a portion of a flowering stem;
FIG. 11 is a portion of a main cane;
FIG. 12 is a specimen of leaf with three leaflets, under surface;
FIG. 13 is a specimen of leaf with seven leaflets, upper surface; and
FIG. 14 is a specimen of leaf with five folioles, under surface.

The characters and properties of this new variety, obtained as indicated above, are thoroughly transmissible by asexual means, i.e. by any method of vegetative propagation, and in particular by grafting an "eye" which will be designated in the trade under the name MElhelvet 0658F, and which will be found on industrial plants as well as on cut stems delivered subsequently in the trade. Thus will be obtained once again the rose variety which is the object of the present invention and whose botanical and descriptive characteristics are given below:

DESCRIPTION

The terminology of the colors corresponds to that of the Horticultural Color Chart of the Royal Horticultural Society.

(A) Plants under glass

Class: Grandiflora
Plant:
*Height.*—1 m. 80 on an average.
*Habit.*—Erect.
Canes:
*Color.*—Young stems: Lettuce Green (H.C.C. 176—a little darker than Tone 861) with a few reddish brown pigmentations. Mature wood: Spinach Green (H.C.C. 187—Tone 0960/1).
*Prickles.*—Shape: straight, slightly inflected towards the base, sometimes a little hooked. Size: medium. Quantity: average, fairly often intermingled with needle-shaped bristles. Color: on young stems; reddish. On mature wood: greenish pink, then straw, then snuff brown.

Leaves:

*Stipules.*—Adnate, pectinate, usually rather narrow and little developed.

*Auricles.*—Fine, short, divergent.

*Petiole.*—Inside: The interior and the edges of the vein are more or less reddish brown in the young foliage, and normal green in the mature foliage. Outside: Light Green, usually with one or several small hooked bristles.

*Folioles.*—Number: 3–5–7, rarely 9. Shape: Elliptical, with a more acuminate point in the young foliage than in the mature foliage. Teeth: Single, more or less even. Texture: Leathery. Appearance as a whole: Dull foliage, average density, fairly large-sized.

*Color.*—Inside: Spinach Green (H.C.C. 187–Tone 0960). Outside: Green, a little rawer than Lavender Green (H.C.C. 196—Tone 000761).

It should be noted that when growth starts, as well as during vegetation, the foliage of the young shoots is Lettuce Green (H.C.C. 176——861/3) with a reddish edge both on the inside and the outside.

Inflorescence:

*Number of flowers.*—In general, one bloom to the stem.

*Peduncle.*—Fairly firm, it shows a few small flimsy prickles, with numerous tiny pedicellate glands. Length: 7 to 10 centimeters. Color: A little darker than Lettuce Green (H.C.C. 176—Tone 861).

*Sepals.*—Normal, pectinate, comparatively narrow, tormentous and whitish green inside, smooth and light green outside.

*Bud.*—Shape: Elongated, somewhat cylindrical. Size: Medium. Color: (When the first petal opens.) Inside: Begonia Rose (H.C.C. 146—Tones 619/1 and 619). Outside: Porcelain Rose (H.C.C. 147—Tone 620/1) with a wide yellowish aureole at the base.

*Flower.*—Form: First of all, elongated, high-centered, the petals of the external border folded in a point, then, when open, protruding petals, overlapping and more or less folded in a point. Double flower. Diameter: 10 to 12 cms. Color:—At the opening: Inside: Porcelain Rose (H.C.C. 147—Tones 620/1 and 620/2 with sheens of Begonia Rose (H.C.C. 146—Tone 619/1) in depth. Outside: Porcelain Rose (H.C.C.147—Tone 620/2) with a wide yellowish white aureole at the base. When fully open: Inside: Porcelain Rose (H.C.C. 147—Tone 620/2) in the center. Camellia Rose (H.C.C.148–Tone 622/2) on the external edge. Outside: Porcelain Rose (H.C.C. 147–Tone 620/3) with a wide yellowish white aureole at the base. Of long duration. Fragrance: Very pronounced fruity odor.

Corolla:

*Petals.*—Texture: Very firm. Shape: The petals of the outer periphery are fairly widely rounded and fold in a point as soon as the flower opens. The petals in the interior of the flower are a little less developed but also fold in a point as the flower gradually opens. The central petals, close to the stamens, are not always entire and show a few whitish median veins as well as fairly pronounced indentations. The unguis is Barium Yellow (H.C.C. 131—Tone 503/2) with a yellowish white aureole. Number: From 25 to 30.

*Stamens.*—Number: 110 on an average. Anthers: Normal, yellowish. Filaments: Evenly placed, but of various lengths, the longest ones are yellowish, the other slightly pinkish. Pistils.—number: 70 average: Stigmas: Normal-yellowish. Styles: More or less strangled and twisted—slightly hairy and yellowish at base—smooth and fuchsin red near the stigmas. Receptacle: Normal-smooth-light Green. Fruit: Rounded-orange yellow.

Development:

*Vegetation.*—Quite vigorous.

*Aptitude for repeat-bloom.*—Excellent.

*Resistance to diseases.*—Very strong.

(B) Plants in the open air (Particular characteristics when compared with plants under glass.)

Plant:

*Height.*—0 m. 80.

*Habit.*—Erect-open.

Canes—Color: Young stems: The reddish brown pigmentations are more pronounced than under glass.

Foliage—folioles:

*Size.*—In general, not as large as that observed under glass.

*Texture.*—Glossy, more leathery.

*Color.*—Upper surface: Spinach Green (H.C.C. 187—darker than Tone 0960). Under surface: Spinach Green (H.C.C. 187—lighter than 0960/3).

Inflorescence:

*Number of flowers.*—In scanty but compact corymbs of 5 to 9 flowers on an average.

*Flower.*—Diameter: From 8 to 10 cms. Color: The same as that observed under glass, except when fully open when it becomes Camellia Rose (H.C.C. 148—Tones 622/2 and 622/1) inside. Peduncle: Length: 5 to 7 cms. Color: More or less reddish brown.

Development:

*Blooming.*—Abundant, intermittent.

*Resistance.*—To Spring frosts: Normal to winter frosts: Very good. To fungus diseases: Especially good.

The plant does not bear many fruits.

I claim:

1. A new rose plant of the grandiflora class substantially as shown and described, characterized by the fact that:

from the physical point of view, the plant, with Spinach Green mature wood, is erect, the flower is double, Porcelain Rose touched up with Begonia Rose in depth, the petals are very firm and folded in a point;

from the biological point of view, the plant is very vigorous, has an excellent aptitude for repeat-blooming, either under glass or outside in the open air, is very resistant to fungus diseases and its flowers last a long time when cut.

No references cited.

ROBERT E. BAGWILL, Primary Examiner